(12) United States Patent
Kold et al.

(10) Patent No.: US 12,702,421 B2
(45) Date of Patent: Aug. 11, 2026

(54) EMBOLIC COIL DELIVERY SYSTEMS AND COMPONENTS WITH FRANGIBLE RELEASE FEATURES

(71) Applicant: Cook Medical Technologies LLC, Bloomington, IN (US)

(72) Inventors: Jens Kold, Jyllinge (DK); Jan Kristoffersen, Næstved (DK); Mikkel Kolding, Sorø (DK); Rana Al-tayar, Brønshøj (DK); Kim Møgelvang Jensen, Frederiksberg (DK)

(73) Assignee: Cook Medical Technologies LLC, Bloomington, IN (US)

( * ) Notice: Subject to any disclaimer, the term of this patent is extended or adjusted under 35 U.S.C. 154(b) by 237 days.

(21) Appl. No.: 18/530,917

(22) Filed: Dec. 6, 2023

(65) Prior Publication Data

US 2024/0180560 A1 Jun. 6, 2024

Related U.S. Application Data

(60) Provisional application No. 63/386,252, filed on Dec. 6, 2022.

(51) Int. Cl.
*A61B 17/12* (2006.01)
*A61B 17/00* (2006.01)

(52) U.S. Cl.
CPC .... *A61B 17/1214* (2013.01); *A61B 17/12113* (2013.01); *A61B 2017/00367* (2013.01); *A61B 2017/12054* (2013.01)

(58) Field of Classification Search
CPC ........ A61B 17/12109; A61B 17/12113; A61B 17/1214; A61B 17/12145; A61B 17/1215; A61B 17/12154; A61B 2017/1205; A61B 2017/12054
See application file for complete search history.

(56) References Cited

U.S. PATENT DOCUMENTS

| | | | | |
|---|---|---|---|---|
| 6,346,091 | B1 | 2/2002 | Jacobsen et al. | |
| 7,722,636 | B2 | 5/2010 | Farnan | |
| 9,149,278 | B2 | 10/2015 | Slazas et al. | |
| 9,339,275 | B2 | 5/2016 | Trommeter et al. | |
| 9,622,754 | B2 | 4/2017 | Ramzipoor et al. | |
| 10,159,489 | B2 | 12/2018 | Bhagchandani et al. | |
| 10,335,155 | B2 | 7/2019 | Beckham et al. | |
| 10,932,933 | B2 | 3/2021 | Bardsley et al. | |
| 2007/0073334 | A1* | 3/2007 | Ramzipoor | A61B 17/12145 606/200 |

(Continued)

*Primary Examiner* — Diane D Yabut
*Assistant Examiner* — Christian D Knauss
(74) *Attorney, Agent, or Firm* — Woodard, Emhardt, Henry, Reeves & Wagner, LLP

(57) ABSTRACT

An embolic coil delivery system includes a delivery shaft that defines a delivery shaft lumen and an embolic coil device that is detachably connected to a distal region of the delivery shaft. The embolic coil device includes coil windings that define a coil lumen. A pull wire is positioned at least partially within the delivery shaft lumen and at least partially within the coil lumen. The pull wire includes a frangible segment that is positioned within the coil lumen. The frangible segment of the pull wire defines a predictable region of separation of the pull wire in response to tensile force so as to detach said embolic coil device from said delivery shaft.

22 Claims, 4 Drawing Sheets

(56) References Cited

U.S. PATENT DOCUMENTS

2009/0062726 A1* 3/2009 Ford ................ A61B 17/12113 606/108
2011/0092997 A1 4/2011 Kang
2012/0035707 A1 2/2012 Mitelberg et al.
2014/0277078 A1* 9/2014 Slazas ................ A61B 17/1214 606/200
2015/0327976 A1 11/2015 Divino et al.
2020/0229957 A1* 7/2020 Bardsley ................. A61F 2/966
2021/0282788 A1 9/2021 Fitz et al.

* cited by examiner

EMBOLIC COIL DELIVERY SYSTEMS AND COMPONENTS WITH FRANGIBLE RELEASE FEATURES

BACKGROUND

The present disclosure relates generally to systems for implanting embolic coil devices for establishing an embolus or vascular occlusion in a patient vessel, and to devices and components useful in such systems.

Embolic coil devices are used to treat a variety of medical conditions, including for example to treat intravascular aneurysms. An embolic coil typically takes the form of a soft, helically wound coil formed by winding wire (e.g. a platinum or platinum alloy wire) about a primary mandrel. In some known forms, the thus-formed coil is then wrapped around a larger, secondary mandrel, and heat treated to impart memory for a secondary shape. The secondary shape can also be imparted by cold forming. Upon delivery from a tubular device such as a catheter to a treatment site, the coil will transition to or toward its more convoluted secondary shape.

Various arrangements are known for detaching the coil from the delivery shaft, including notably electrolytic and mechanical detachment arrangements. Many known mechanical detachment arrangements have a delivery shaft defining a lumen and a pull wire (also termed a "release" wire) that interfaces with a feature of the coil device and that can be moved proximally in the shaft lumen to cause detachment of the embolic coil device.

There remain needs for embolic coil delivery systems that incorporate detachment features that are conducive to manufacture and that are easy and reliable in use. Aspects of the present disclosure are addressed to these needs.

SUMMARY

In some aspects, provided are systems for delivering an embolic coil device. The systems may include a flexible elongate delivery shaft having a distal region and defining a delivery shaft lumen. An embolic coil device may be detachably connected to said distal region of said elongate delivery shaft. The embolic coil device may also include coil windings that define a coil lumen. An elongate pull wire, which may be metallic, may be positioned at least partially within said delivery shaft lumen and at least partially within said coil lumen. The pull wire may include a proximal segment, a frangible segment, and a distal segment. The frangible segment may be positioned within said coil lumen and be distal of said delivery shaft. The frangible segment of said pull wire may define a predictable region of separation of the pull wire in response to tensile force so as to detach the embolic coil device from the delivery shaft.

The distal segment of the pull wire is distal of the frangible segment. The distal segment of the pull wire may be attached to the embolic coil device at the distal coil tip of the embolic coil device. In some instances, the distal segment of the pull wire may also be attached to the embolic coil device at a second location that is distal of the frangible segment. For some embodiments, the distal segment of the pull wire may be welded to the embolic coil device.

The frangible segment of the pull wire may have a cross-sectional dimension that is smaller than a cross-sectional dimension of the proximal segment of the pull wire immediately proximal of the frangible segment. The cross-sectional dimension of the frangible segment may also be smaller than a cross-sectional dimension of the distal segment immediately distal of the frangible segment.

In some instances, the delivery shaft may include a breakable section at which the delivery shaft is configured to selectively break and separate in response to bending forces applied across the pull wire attachment location of the delivery shaft.

Some aspects may include a method of delivering an embolic coil device. The method includes guiding the embolic coil device, which is detachably connected to a delivery shaft, to a desired location in the vasculature of a patient. The embolic coil device includes coil windings that define a coil lumen. A tensile force is applied to a pull wire including a frangible segment that is positioned at least partially within a delivery shaft lumen defined by said delivery shaft and at least partially within said coil lumen. The frangible segment of said pull wire defines a predictable region of separation of the pull wire in response to the tensile force so as to detach the embolic coil device from said delivery shaft. The delivery shaft may then be retracted from the vasculature of the patient, while the embolic coil device remains within the vasculature of the patient. Systems for delivering an embolic coil device as described above and elsewhere herein can be used in the practice of such methods.

Additional embodiments herein, as well as features and advantages of embodiments described herein, will be apparent to those skilled in the field from the descriptions herein.

DETAILED DESCRIPTION

Figure 1:
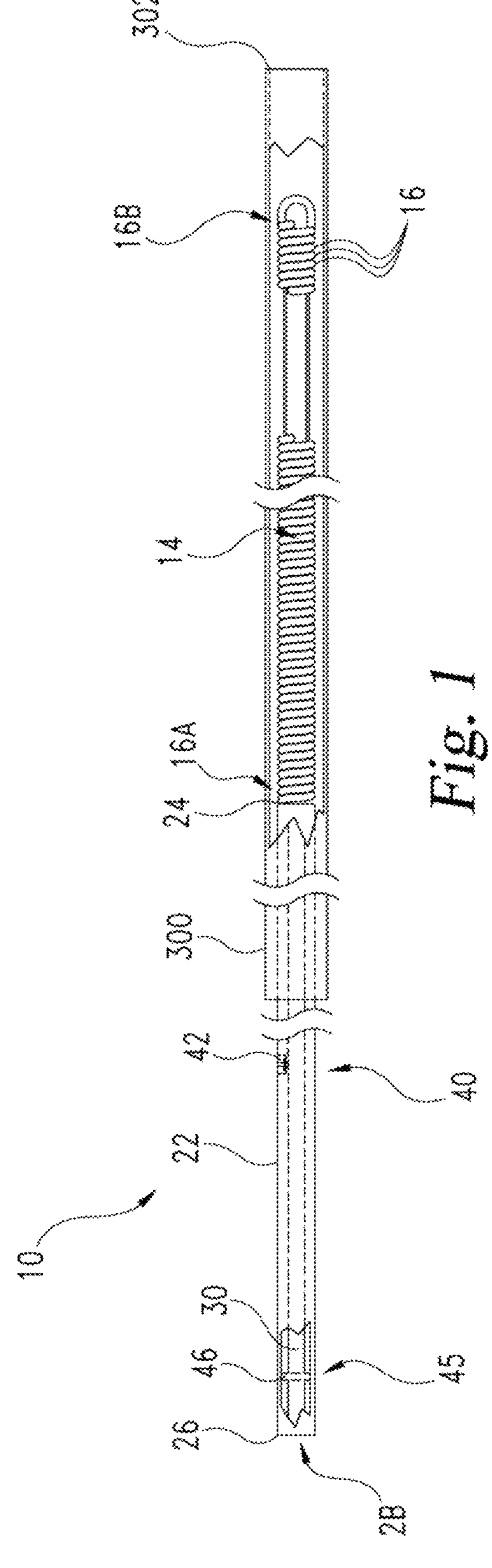
FIG. 1 is an illustration of one embodiment of an embolic coil delivery system herein received within a catheter with portions of the catheter cut away to display system components therein.

Reference will now be made to certain embodiments, some of which are illustrated in the drawings, and specific language will be used to describe the same. It will nevertheless be understood that no limitation of the scope of the disclosure is thereby intended. Any alterations and further modifications in the described embodiments and any further applications of the principles as described herein are contemplated as would normally occur to one skilled in the art to which this disclosure relates.

As disclosed above, aspects of the present disclosure relate to systems for delivering an embolic device to a patient, and related devices, components and methods. The systems can include an elongate delivery shaft and an embolic device, for example an embolic coil device, detachably connected to a distal region of the delivery shaft, wherein the medical device can be detached from the delivery shaft by proximal movement of a pull wire.

As used herein, the term "proximal" means close to the operator and the term "distal" means away from the operator.

Spatially relative terms such as "lower", "upper", "under", "over", "above" and the like may be used to describe and element's and/or feature's relationship to another element(s) or feature(s), for example as depicted in the Figures. It will be understood that the spatially relative terms are intended to encompass different operations of the system, device or component in use in addition to the orientation described or depicted in the Figures. For example, if a device or component as depicted in the Figures is inverted, an element that is shown and described as "upper" would then be oriented as "lower".

Turning now to the Figures, FIG. 1 illustrates a delivery system 10 for delivering an embolic coil device 14 to a vascular space such as an aneurysm, received within the lumen of a catheter 300. The embolic coil device 14 may having a plurality of coil windings 16 extending from a proximal end 16A to a distal end 16B. Typically, the coil windings 16 are made from wire, with the wire usually made of a metal such as a platinum, a platinum alloy, or a superelastic metal alloy (e.g. a superelastic nickel/titanium alloy such as nitinol). The diameter of the wire forming the coil windings 16 may be in the range of about 0.005 mm to about 0.15 mm. The coil formed by coil windings 16 may have an outer primary diameter of between about 0.075 and about 1 mm and in some forms will have an outer primary diameter of between about 0.2 mm and about 0.5 mm, especially those embolic coil devices 14 intended for use in neurovascular applications.

The axial length of the embolic coil device 14 will usually fall in the range of around 0.5 to around 100 cm, more usually around 2 to 50 cm. It will be understood, however, that other axial lengths may be employed depending on the application. As well, it will be understood that the embolic coil device 14 may have a thrombogenic material such as fibers (not shown) connected to the coil windings 16 to enhance its thrombogenicity, and that other embolic coil devices described herein may also similarly include such a thrombogenic material. Some embodiments of the embolic coil device may include j-shape, tornado, and/or straight coils to form the coil windings 16. The coils may be made with fibers or without fibers.

The delivery system 10 also includes a flexible elongate delivery shaft 22 having a distal end 24, a proximal end 26, and a delivery shaft lumen 28 therebetween. The delivery shaft 22 may be formed from any suitable material, including as examples polymeric materials, metal materials, or combinations thereof. Metal hypotube materials such as stainless steel hypotube or nitinol hypotube material may be used. As illustrative polymer materials, flexible and lubricious materials such as polyimide, polytetrafluoroethylene (PTFE), polyetheretherketone (PEEK), fluorinated ethylene propylene (FEP), or the like, may be used. As well, combinations of different metal hypotube materials, such as a combination including a first stainless steel hypotube segment attached (e.g. welded) to a second, different stainless steel hypotube segment can typically be used. For example, the second stainless steel hypotube segment may be positioned distal to, and may be more flexible and/or shorter than, the first hypotube segment. This can provide an overall delivery shaft 22 that is more flexible in its distal region than in its proximal region. Combinations of other materials that provide a more flexible distal region and a less flexible proximal region can also be used in some forms.

Metal hypotube materials, and thus the segments of the delivery shaft 22 made from them, can in some aspect have internal diameters in the range of about 0.5 to about 0.9 mm and/or external diameters in the range of about 0.6 to about 1 mm. In some preferred small diameter forms, such hypotube materials will have internal diameters in the range of about 0.1 to about 0.4 mm and/or external diameters in the range of about 0.2 to about 0.5 mm. The wall thickness of the hypotube materials, between the internal and the external diameter, can range from about 0.05 to about 0.25 mm.

The delivery shaft 22 will generally have a length between the distal end 24 and the proximal end 26 that permits the shaft to be advanced intravascularly to the target site for delivery of the embolic coil device 14 while leaving the proximal end 26 positioned outside of the patient's body. For example, the delivery shaft 22 can have a length in the range of about 1 to about 2 meters.

With reference particularly to FIGS. 1-4, the delivery system 10 also includes an elongate pull wire 30 disposed within the delivery shaft lumen 28 of the delivery shaft 22. The elongate pull wire 30 has a proximal end 31 and a distal end 38 (see FIG. 2). As an example, the elongate pull wire 30 may be formed from one or more polymeric or metal materials, or combinations thereof. The pull wire 30 may be formed from a metal such as nitinol, titanium, titanium alloy, platinum, stainless steel or the like. The pull wire 30 has a diameter that is less than the diameter of the delivery shaft lumen 28 of the elongate delivery shaft 22. In one exemplary embodiment, the pull wire 30 is formed from nitinol, optionally coated with a lubricous polymer such as polytetrafluoroethylene (PTFE) and has an outer diameter of about 0.1 mm.

The delivery system 10 may also include an arrangement for protecting against unintended proximal retraction of the pull wire 30 that may cause unintended release of the embolic coil device 14. As illustrated in FIG. 1, at a first location 45, the delivery shaft 22 is attached to the pull wire 30. This attachment can, for example, be provided by an amount of adhesive 46, although other attachments such as welds or frictional engagements provided by one or more crimps of the delivery shaft 22 against the outer surface of the pull wire 30 may be used. This attachment fixes the relative positions of the delivery shaft 22 and pull wire 30. At a second location 40 distal of the first location 45, the delivery shaft 22 has a section 42 at which the delivery shaft 22 is configured to selectively break and separate in response to bending forces applied across the first location 45 (as compared to the sections of delivery shaft 22 that flank first location 45 on either side). After this, the separated proximal piece of delivery shaft 22, which is attached the pull wire 30 at location 45, can be moved (e.g. pulled) proximally so as to retract pull wire 30 proximally within delivery shaft lumen 28 in a sliding movement and thereby cause detachment of the embolic coil device 14, as will be discussed in more detail below. In this manner, the delivery system 10 can be used to advance the embolic coil device 14 to a desired target location in the vasculature of the patient, after which the delivery shaft 22 can be broken and separated at location 40 and the separated proximal piece of delivery shaft 22 can be pulled proximally to cause detachment of the embolic coil device 14.

Figure 2:
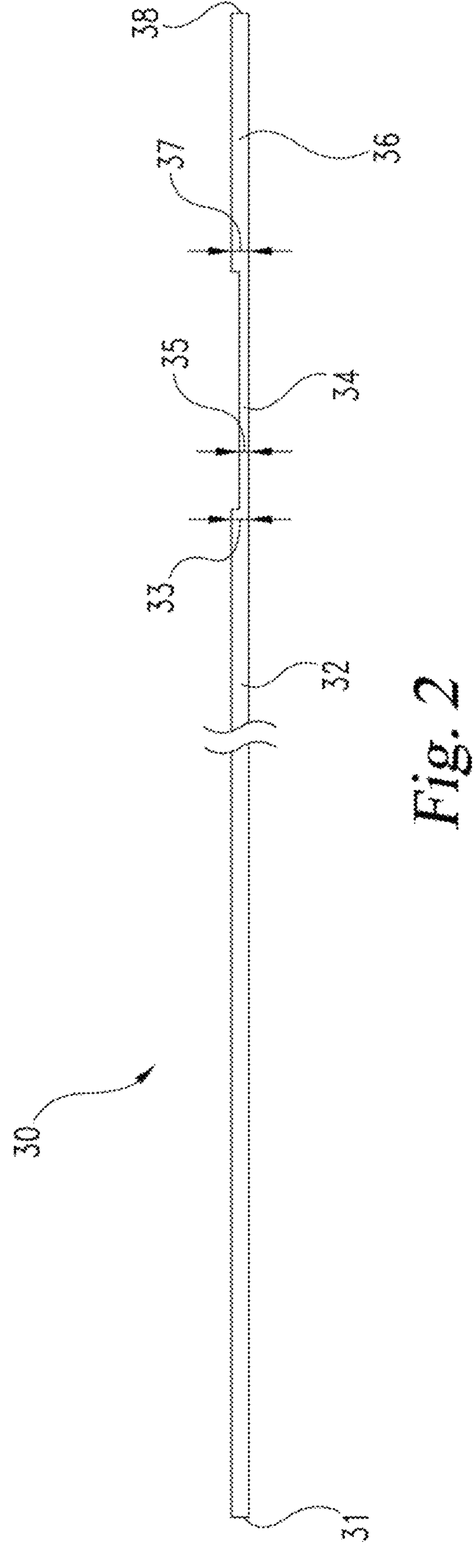
FIG. 2 is a side view of a pull wire of the embolic coil delivery system of FIG. 1.
Figure 3:
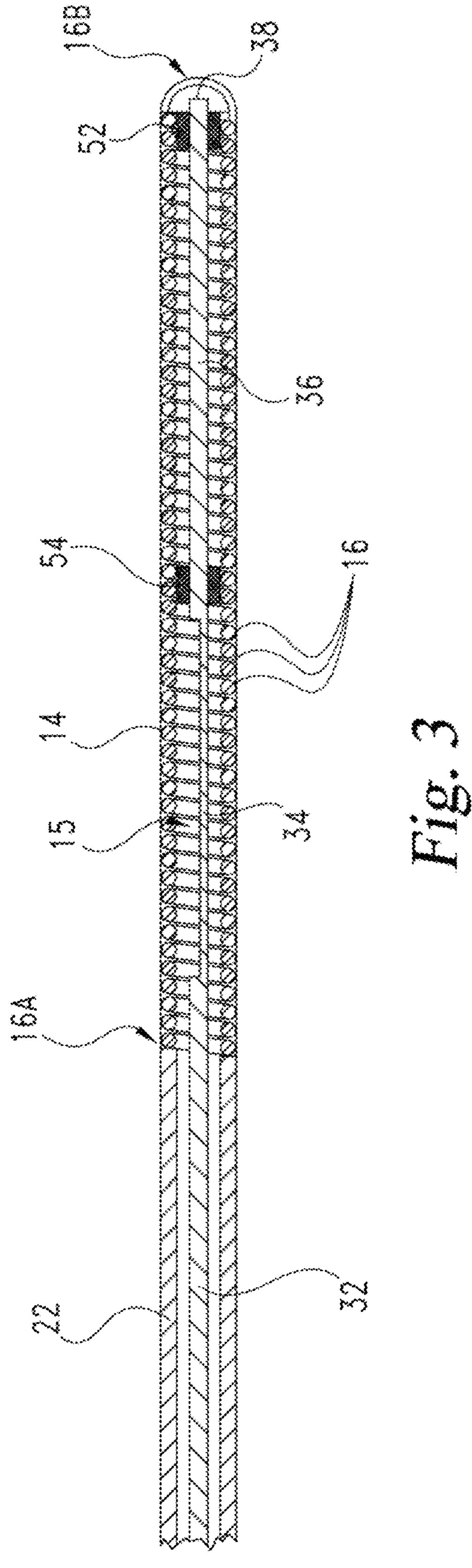
FIG. 3 is a partial cross-sectional view of the embolic coil delivery system of FIG. 1 before the pull wire has been broken.

The pull wire 30 is shown in greater detail in FIG. 2. As shown, the pull wire 30 includes a proximal segment 32, a frangible segment 34, and a distal segment 36. FIG. 3 only shows a portion of proximal segment 32, as the proximal segment 32 has a length that extends the length of the delivery shaft 22 so that the proximal segment of the pull wire 30 may be accessed by a user. While in the illustrated embodiment the pull wire 30 is formed from a single length of wire, it will be understood that in other embodiments the pull wire 30 may be formed from multiple lengths of wire, of the same or different composition, that are connected (e.g. welded or bonded) to one another.

As illustrated, the frangible segment 34 has a cross-sectional dimension 35 that is smaller than a cross-sectional dimension 33 of the proximal segment 32 of the pull wire 30 that is immediately proximal of the frangible segment 34. Additionally, the cross-sectional dimension 35 of the frangible segment 34 is smaller than a cross-sectional dimension 37 of the distal segment 36 that is immediately distal of the frangible segment 34. In some instances, the cross-sectional dimension 33 of the proximal segment 32 may be equal to the cross-sectional dimension 37 of the distal segment 36. The smaller diameter of the frangible segment 34 defines a predictable region of separation on the pull wire 30 in response to tensile force applied to the pull wire 30 so as to detach the embolic coil device 14 from the delivery shaft 22. It will be understood that the frangible segment 34 may be configured for predictable breakage in other manners (e.g. it may be compositionally different from other portions of pull wire 30 and/or include a breakable weld or other connection between otherwise separate wire segments forming pull wire 30), in addition to or as an alternative to a difference in diameter as disclosed in connection with FIGS. 1-4 herein.

A partial cross-sectional view of the pull wire 30 positioned within the delivery shaft lumen 28 and within the embolic coil lumen 15 is shown in FIG. 3. In the illustrated embodiment, the frangible segment 34 is positioned distal of the distal end 24 of delivery shaft 22. Also, as illustrated, the distal segment 36 of the pull wire 30 may be attached to the distal end 16B of the coil windings 16 of the embolic coil device 14 at an attachment point 52. In some embodiments, the distal segment 36 may be attached to the coil windings 16 by a weld, but in other embodiments, adhesive or any other suitable forms of attachment may be used. The distal segment 36 may also be attached to the coil windings 16 at an additional attachment point 54 positioned distally of said frangible segment 34. In some embodiments the distal segment 36 may be attached to the coil windings 16 at attachment point 54 by a weld, but in other embodiments, adhesive or any other suitable forms of attachment may be used. In some embodiments, the attachment point 54 may be distal of and immediately adjacent to the distalmost end of the frangible segment 34 of the pull wire 30, or in some forms distal of and within about 15 mm, or within about 10 mm, or within about 5 mm, of the distalmost end of the frangible segment 34 of the pull wire 30.

By attaching to the embolic coil device 14 at two different locations, the distal segment 36 of the pull wire 30 acts as a stretch resistant element that assists to reduce the risk of stretching of the coil windings 16 of the embolic coil device 14 after deployment in the desired vascular space. Attachment of the distal segment 36 at attachment point 54 can also isolate tension applied to the pull wire 30 to portions of the pull wire 30 that are proximal of attachment point 54 which may aide the performance of the tension-induced breakage of the pull wire 30 at the frangible segment 34. It will be understood that while the illustrated embodiment has two attachment points 52 and 54 to the coil windings 16, additional points of attachment of the pull wire 30 to the coil windings could be included, for example at one or more additional points between attachment points 52 and 54.

Figure 4:
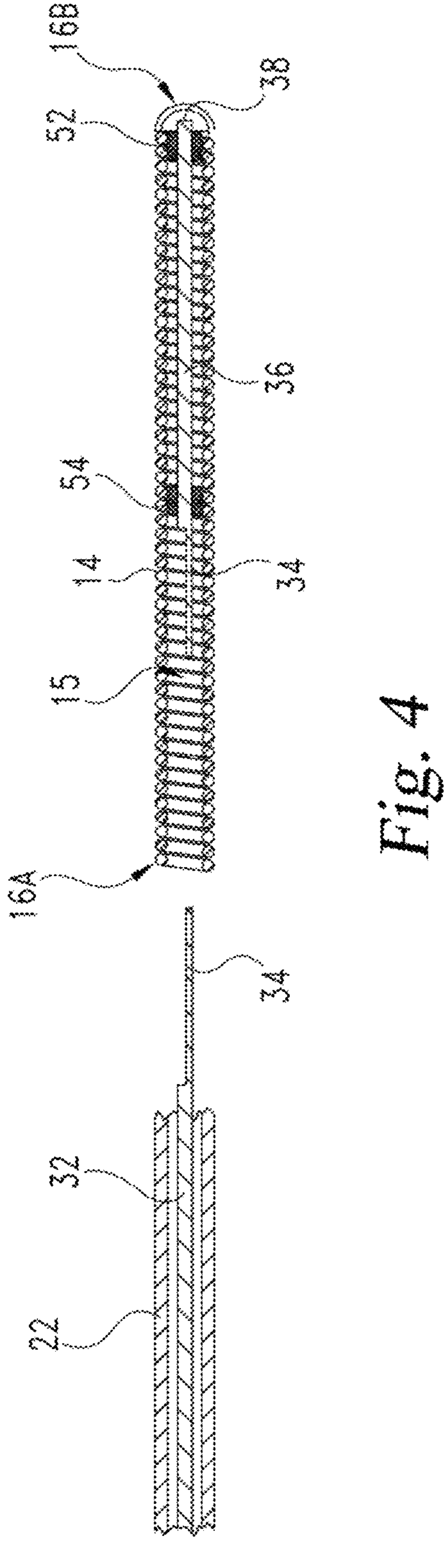
FIG. 4 is a partial cross-sectional view of the embolic coil delivery system of FIG. 1 after the pull wire has been broken.

A partial cross-sectional view of the delivery system 10 after the pull wire 30 has been broken and the delivery shaft 22 is separated from the embolic coil device 14 is shown in FIG. 4. The pull wire 30 breaks at a location on the frangible segment 34 of the pull wire 30, for example because this is the location that the pull wire 30 has the smallest cross-sectional dimension. The proximal segment 32 and a portion of the frangible segment 34 of the pull wire 30 is removed from the embolic coil device 14 with the delivery shaft 22. The distal segment 36 of the pull wire 30 and the other portion of the frangible segment 34 remains in the embolic coil lumen 15 of the embolic coil device 14. The coil windings 16 of the embolic coil device 14 surround the broken end of the frangible segment 34 of the pull wire 30 to isolate the broken end of the frangible segment 34 from undesired interaction with tissue of the patient.

A method of using the delivery system 10 to deliver the embolic coil device 14 to an aneurysm in a blood vessel is described below. The catheter 300 (e.g. microcatheter) can be positioned within the vessel so as to place its distal end 302 within the aneurysm. The delivery system 10 including the delivery shaft 22 and the detachably connected embolic coil device 14 is then guided through the catheter 300 to the desired location in the vasculature of the patient. The delivery system 10 may be pre-loaded in an introducer sheath or the like (not shown). The delivery system 10 is then advanced to place the embolic coil device 14 in the aneurysm. One or more radiopaque markers located on the delivery system 10 and/or catheter 300 may be used to aid the physician in positioning the delivery system 10 for deployment of the embolic coil device 14.

The embolic coil device 14 can then be released into the aneurysm by applying a tensile force on the pull wire 30 with enough force to cause the pull wire 30 to break at the frangible segment 34, which provides a predictable region of separation of the pull wire 30. Where the delivery system 10 includes an arrangement for protecting against unintended release of the embolic coil device 14 as discussed above, prior to proximal retraction of the pull wire 30, the delivery shaft 22 is broken at location 40 by applying bending forces to the delivery shaft 22 across location 40.

Breaking the pull wire 30 at the frangible segment 34 allows the embolic coil device 14 to separate from the delivery shaft 22. The broken portion of the frangible segment 34 remains within the coil windings 16 of the embolic coil device 14 so that the broken portion remains surrounded by the coil windings 16 even after the embolic coil device 14 is released. This prevents the broken portion of the frangible segment 34 from damaging the vascular walls of the patient as the embolic coil device 14 is placed in and remains at the desired location within the vascular system. The delivery shaft may be retracted from the vasculature of the patient, leaving only the embolic coil device in the aneurysm.

The following numbered clauses set out specific embodiments that may be useful in understanding the present invention:

1. A system for delivering an embolic coil device, comprising:
   - a flexible elongate delivery shaft having a distal region and defining a delivery shaft lumen;
   - an embolic coil device detachably connected to said distal region of said elongate delivery shaft, wherein said embolic coil device includes coil windings that define a coil lumen;
   - an elongate pull wire positioned at least partially within said delivery shaft lumen and at least partially within said coil lumen, wherein said pull wire includes a frangible segment positioned within said coil lumen; and
   - wherein said frangible segment of said pull wire defines a predictable region of separation of the pull wire in response to tensile force applied to the pull wire so as to detach said embolic coil device from said delivery shaft.

2. The system for delivering an embolic coil device of clause 1,
wherein said pull wire includes a distal segment that is distal of said frangible segment, wherein said distal segment of said pull wire is attached to said embolic coil device at a distal end of said embolic coil device.
3. The system for delivering an embolic coil device of clause 2, wherein the distal segment is attached to said embolic coil device by a weld.
4. The system for delivering an embolic coil device of any one of clauses 2 to 3,
wherein said distal segment is attached to said embolic coil device at a second location distal of said frangible segment.
5. The system for delivering an embolic coil device of clause 4, wherein the distal segment is attached to said embolic coil device at said second location by a weld.
6. The system for delivering an embolic coil device of any one of clauses 1 to 5, wherein said pull wire is metallic.
7. The system for delivering an embolic coil device of any one of clauses 2 to 6,
wherein said frangible segment has a cross-sectional dimension that is smaller than a cross-sectional dimension of a proximal segment of said pull wire immediately proximal of said frangible segment; and
wherein said frangible segment has a cross-sectional dimension that is smaller than a cross-sectional dimension of said distal segment immediately distal of said frangible segment.
8. The system for delivering an embolic coil device of any one of clauses 1 to 7, wherein said pull wire is attached to said delivery shaft at a pull wire attachment location.
9. The system for delivering an embolic coil device of clause 8, wherein said delivery shaft includes a breakable section at which said delivery shaft is configured to selectively break and separate in response to bending forces applied across said pull wire attachment location of said delivery shaft.
10. The system for delivering an embolic coil device of any one of clauses 1 to 9, wherein said coil windings are helical.
11. An embolic coil device for detachable connection to an elongate delivery shaft of an embolic coil delivery system, comprising:
coil windings, wherein said coil windings define a coil lumen;
a pull wire extending within said coil lumen;
wherein said pull wire includes a frangible segment positioned within said coil lumen; and
wherein said pull wire includes a distal segment that is distal of said frangible segment, wherein said distal segment is attached to said coil windings at a distal coil tip of said coil windings.
12. The system for delivering an embolic coil device of clause 11, wherein the distal segment is attached to said distal coil tip of said coil windings by a weld.
13. The system for delivering an embolic coil device of any one of clauses 11 to 12,
wherein said distal segment attached to said coil windings at a second location immediately adjacent to said frangible segment.
14. The embolic coil device of clause 13, wherein the distal segment is attached to said embolic coil device at said second location by a weld.
15. The embolic coil device of any one of clauses 11 to 14, wherein said coil windings are helical.
16. The embolic coil device of any one of clauses 11 to 15, wherein said pull wire further comprises a proximal segment extending immediately proximally from said frangible segment.
17. The embolic coil device of clause 16, wherein said frangible segment has a cross-sectional dimension that is smaller than a cross-sectional dimension of said proximal segment of said pull wire immediately proximal of said frangible segment.
18. The embolic coil device of any one of clauses 16 to 17, wherein said distal segment of said pull wire has a cross-sectional dimension that is equal to the cross-sectional dimension of said proximal segment of said pull wire.
19. The embolic coil device of any one of clauses 11 to 18, wherein said frangible segment has a cross-sectional dimension that is smaller than a cross-sectional dimension of said distal segment of said pull wire immediately distal of said frangible segment.
20. The embolic coil device of any one of clauses 11 to 19, wherein said pull wire is metallic.
21. A method comprising:
guiding an embolic coil device detachably connected to a delivery shaft by a pull wire to a desired location in a vasculature of a patient, wherein said embolic coil device includes coil windings that define a coil lumen, and wherein the pull wire is positioned at least partially within a delivery shaft lumen defined by said delivery shaft and at least partially within said coil lumen;
applying a tensile force to said pull wire to break said pull wire at a frangible segment of said pull wire positioned within said coil lumen, so as to detach said embolic coil device from said delivery shaft.
22. The method of clause 21, further comprising:
retracting said delivery shaft from the vasculature of the patient.

The uses of the terms “a” and “an” and “the” and similar references herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate embodiments of the disclosure and does not pose a limitation on the scope of the disclosure unless otherwise claimed. No language in the specification should be construed as indicating any non-claimed element as essential to the practice of the products or methods defined by the claims.

While embodiments of the disclosure have been illustrated and described in detail in the drawings and foregoing description, the same is to be considered as illustrative and not restrictive in character, it being understood that only some embodiments have been shown and described and that all changes and modifications that come within the spirit of the disclosures herein are desired to be protected.

The invention claimed is:

1. A system for delivering an embolic coil device, comprising:

a flexible elongate delivery shaft having a distal region and defining a delivery shaft lumen;

an embolic coil device detachably connected to said distal region of said elongate delivery shaft, wherein said embolic coil device includes coil windings that define a coil lumen;

an elongate pull wire positioned at least partially within said delivery shaft lumen and at least partially within said coil lumen, wherein said pull wire includes a frangible segment positioned within said coil lumen; and wherein said frangible segment of said pull wire defines a predictable region of separation of the pull wire in response to tensile force applied to the pull wire so as to detach said embolic coil device from said delivery shaft.

2. The system for delivering an embolic coil device of claim 1, wherein said pull wire includes a distal segment that is distal of said frangible segment, wherein said distal segment of said pull wire is attached to said embolic coil device at a distal end of said embolic coil device.

3. The system for delivering an embolic coil device of claim 2, wherein the distal segment is attached to said embolic coil device by a weld.

4. The system for delivering an embolic coil device of claim 2, wherein said distal segment is attached to said embolic coil device at a second location distal of said frangible segment.

5. The system for delivering an embolic coil device of claim 4, wherein the distal segment is attached to said embolic coil device at said second location by a weld.

6. The system for delivering an embolic coil device of claim 2, wherein said frangible segment has a cross-sectional dimension that is smaller than a cross-sectional dimension of a proximal segment of said pull wire immediately proximal of said frangible segment; and wherein said frangible segment has a cross-sectional dimension that is smaller than a cross-sectional dimension of said distal segment immediately distal of said frangible segment.

7. The system for delivering an embolic coil device of claim 1, wherein said pull wire is metallic.

8. The system for delivering an embolic coil device of claim 1, wherein said pull wire is attached to said delivery shaft at a pull wire attachment location.

9. The system for delivering an embolic coil device of claim 8, wherein said delivery shaft includes a breakable section at which said delivery shaft is configured to selectively break and separate in response to bending forces applied across said pull wire attachment location of said delivery shaft.

10. The system for delivering an embolic coil device of claim 1, wherein said coil windings are helical.

11. An embolic coil device for detachable connection to an elongate delivery shaft of an embolic coil delivery system, comprising:

coil windings, wherein said coil windings define a coil lumen;

a pull wire extending within said coil lumen;

wherein said pull wire includes a frangible segment positioned within said coil lumen; and wherein said pull wire includes a distal segment that is distal of said frangible segment, wherein said distal segment is attached to said coil windings at a distal coil tip of said coil windings.

12. The system for delivering an embolic coil device of claim 11, wherein the distal segment is attached to said distal coil tip of said coil windings by a weld.

13. The system for delivering an embolic coil device of claim 11, wherein said distal segment is attached to said coil windings at a second location immediately adjacent to said frangible segment.

14. The embolic coil device of claim 13, wherein the distal segment is attached to said embolic coil device at said second location by a weld.

15. The embolic coil device of claim 11, wherein said coil windings are helical.

16. The embolic coil device of claim 11, wherein said pull wire further comprises a proximal segment extending immediately proximally from said frangible segment.

17. The embolic coil device of claim 16, wherein said frangible segment has a cross-sectional dimension that is smaller than a cross-sectional dimension of said proximal segment of said pull wire immediately proximal of said frangible segment.

18. The embolic coil device of claim 16, wherein said distal segment of said pull wire has a cross-sectional dimension that is equal to the cross-sectional dimension of said proximal segment of said pull wire.

19. The embolic coil device of claim 11, wherein said frangible segment has a cross-sectional dimension that is smaller than a cross-sectional dimension of said distal segment of said pull wire immediately distal of said frangible segment.

20. The embolic coil device of claim 11, wherein said pull wire is metallic.

21. A method comprising:

guiding an embolic coil device detachably connected to a delivery shaft by a pull wire to a desired location in a vasculature of a patient, wherein said embolic coil device includes coil windings that define a coil lumen, and wherein the pull wire is positioned at least partially within a delivery shaft lumen defined by said delivery shaft and at least partially within said coil lumen; and applying a tensile force to said pull wire to break said pull wire at a frangible segment of said pull wire positioned within said coil lumen, so as to detach said embolic coil device from said delivery shaft.

22. The method of claim 21, further comprising:

retracting said delivery shaft from the vasculature of the patient.

* * * * *